United States Patent [19]

Ikematsu et al.

[11] Patent Number: 4,707,864
[45] Date of Patent: Nov. 24, 1987

[54] SANITARY URINE COLLECTING APPARATUS

[76] Inventors: Hideaki Ikematsu, 7-12-17 Suzurandai-kitamachi, Kita-ku, Kobe 651-11; Masako Kawamoto, 2-3-45 Ohtsuka, Miki 673-04, both of Japan

[21] Appl. No.: 835,100

[22] Filed: Feb. 28, 1986

[30] Foreign Application Priority Data

Mar. 2, 1985 [JP] Japan .................................. 60-41556

[51] Int. Cl.⁴ .............................................. A47K 11/00
[52] U.S. Cl. ..................................................... 4/144.3
[58] Field of Search ............................. 604/327–331; 128/760, 761, 763, 767, 769; 4/144.1–144.4; 294/1.4, 1.5

[56] References Cited

U.S. PATENT DOCUMENTS

| 3,030,636 | 4/1962 | Evans | 4/144.3 |
| 4,050,103 | 9/1977 | Nakao et al. | 4/144.3 |
| 4,121,306 | 10/1978 | Bringman | 4/144.3 |
| 4,149,745 | 4/1979 | Willis | 294/1.4 |
| 4,457,314 | 7/1984 | Knowles | 604/327 |

FOREIGN PATENT DOCUMENTS 52-70798  5/1977  Japan .

OTHER PUBLICATIONS

Page of a catalog published by Konbi Anraku Nyoki K.K., date unknown.

Primary Examiner—C. Fred Rosenbaum
Assistant Examiner—J. L. Kruter
Attorney, Agent, or Firm—Marshall, O'Toole, Gerstein, Murray & Bicknell

[57] ABSTRACT

A sanitary device comprising a urine receiver and a urine bag removably attached to the receiver. The urine reciever includes a receiver body forming an opening at least at both ends thereof, and adapted to accommodate the urine bag therein through the open ends. A receiver frame is adapted to rotatably support the receiver body by means of pivot pins and is equipped with grip means at a lower end thereof, adapted to press one side of the receiver body in abutment against the body of a user of the device. A grip handle portion is disposed at the upper end thereof. The urine bag is a hollow element having an opening at one end thereof and fitted with an elastic, hygroscopic abutting member configured to be complementary for the inguinal region of the body against which it is to be abutted, and it is adapted to be accommodated in the receiver body to thereby prevent leakage of urine during use of the device.

12 Claims, 7 Drawing Figures

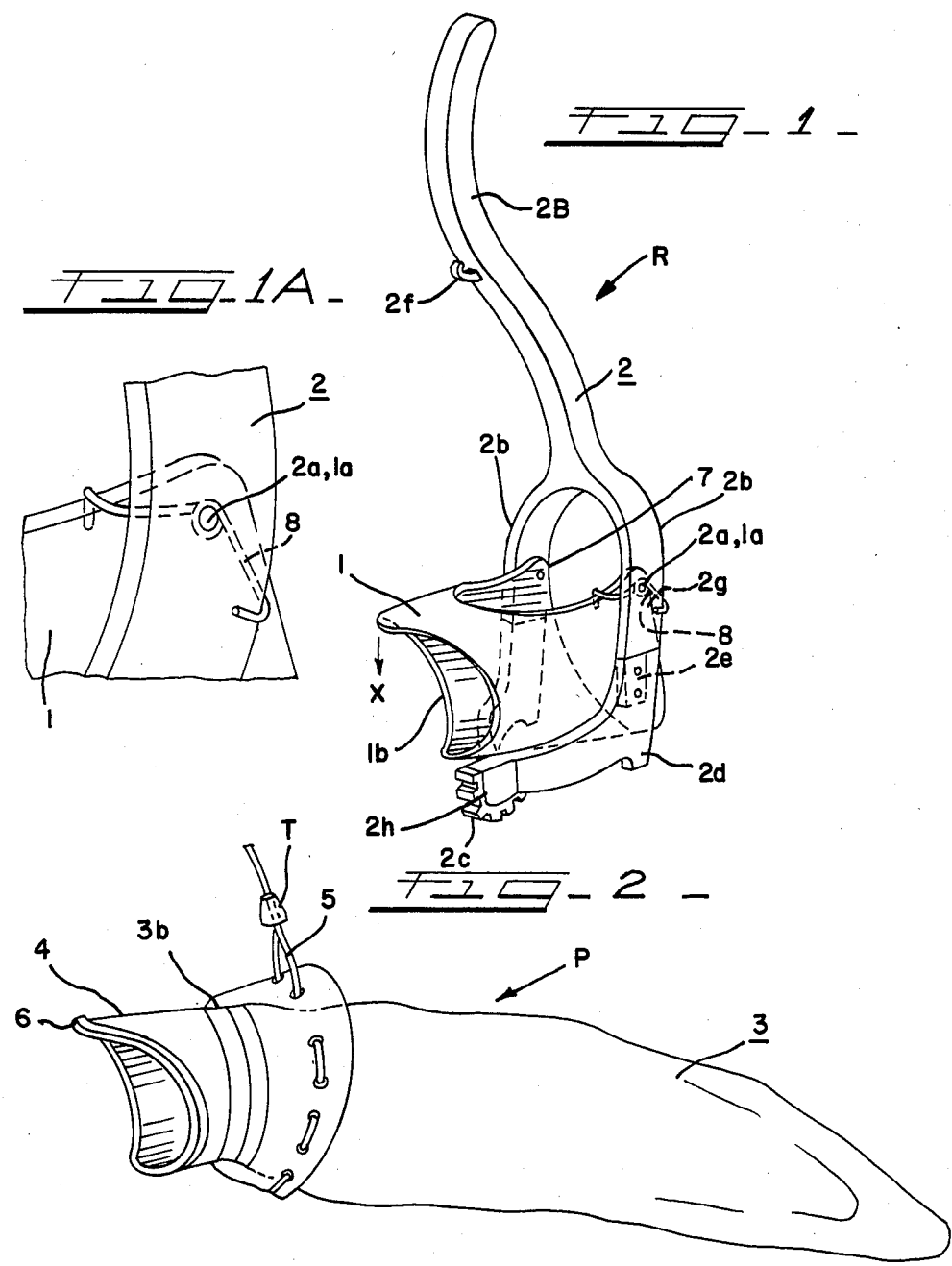

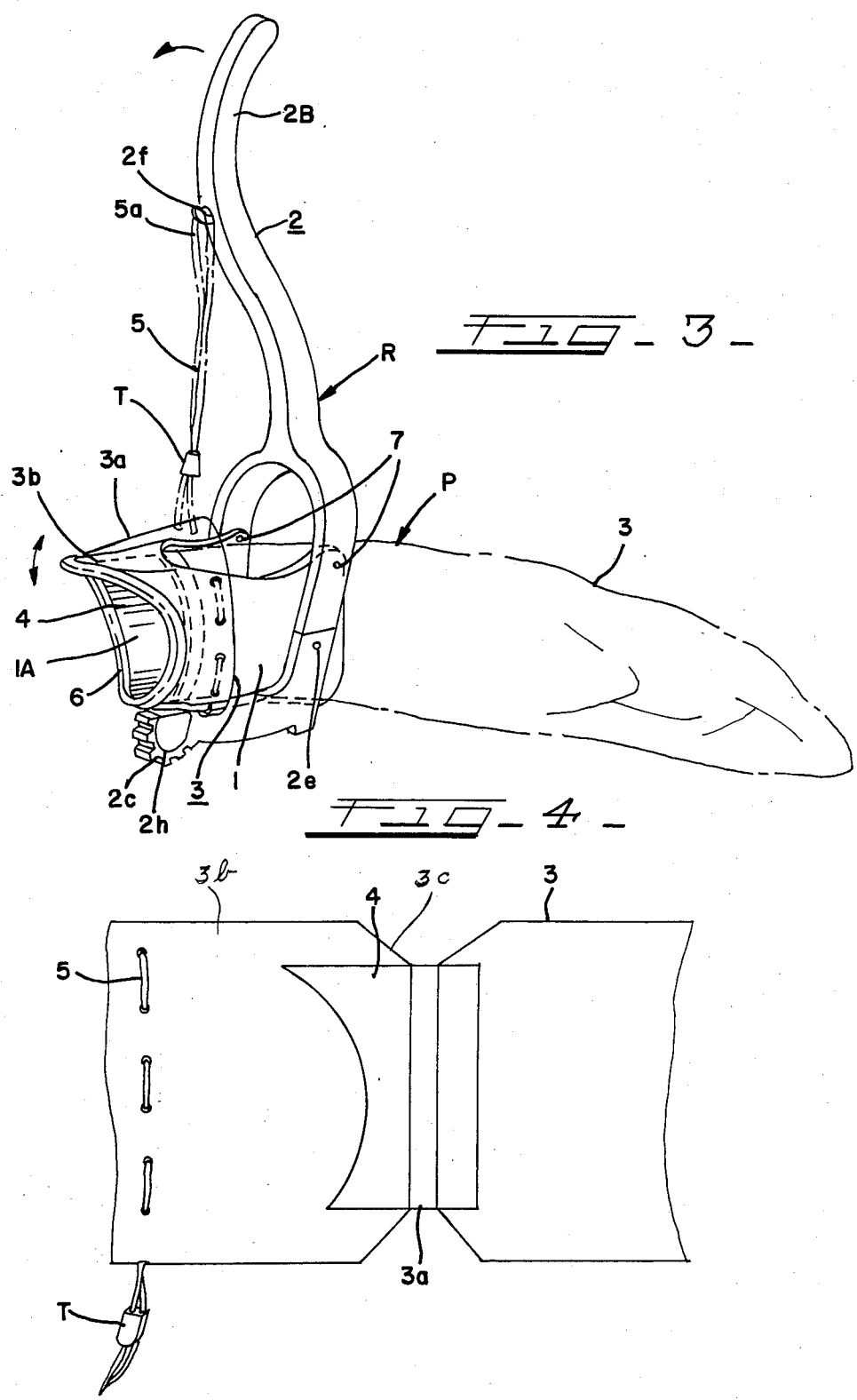

U.S. Patent  Nov. 24, 1987  Sheet 3 of 3  4,707,864
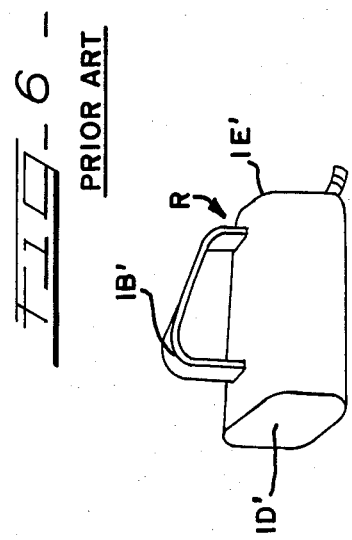
FIG-6
PRIOR ART
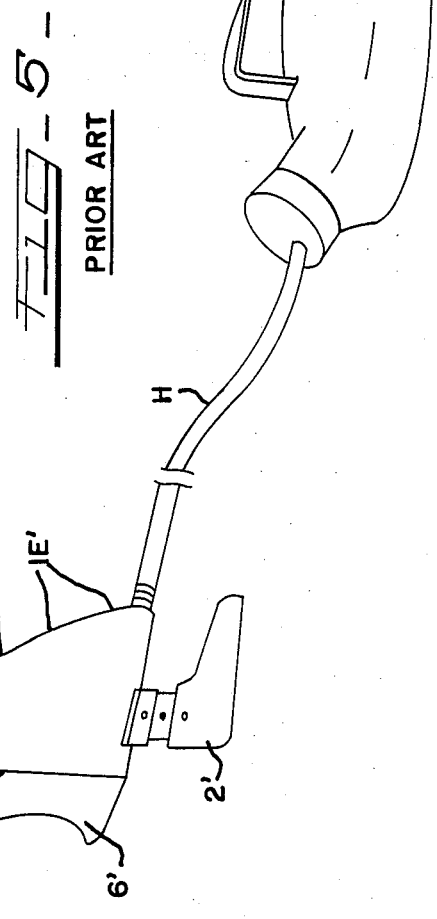
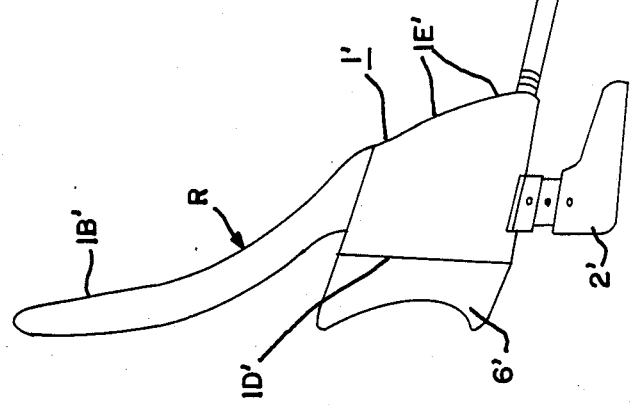
FIG-5
PRIOR ART

2

SANITARY URINE COLLECTING APPARATUS

FIELD AND BACKGROUND OF THE INVENTION

The present invention relates to a sanitary device for patients and elderly persons (hereinafter, both are referred to as the patient) which can be used for collecting urine while the patient is in the lying position on a bed.

Any sanitary device for use by a patient who is confined to a bed must be constructed such that the patient can use it easily while reclining and such that the use of the device does not result in soiling of the clothes, linen and the like.

There have been available a variety of such devices for collecting urine but none has proved to completely meet the above-mentioned requirements. Aside from the sanitary devices for males, the conventional devices for females are not satisfactory because the physical features of the female groin do not easily permit complete recovery of the urine into a sanitary device without contamination of the clothes, linen and etc. with spilt urine.

Recently, in consideration of the human dignity and privacy of the patient, it has been demanded that a sanitary device be provided which the patient can use personally without the help of a nurse, can use repeatedly without cleaning, (thus saving labor in the hospital or at home), and permits easy disposal of the urine.

The latest known devices available for this purpose are shown in FIGS. 5 and 6. Such a device generally includes a receiver R which is applied against the body, a urine collecting tank P' and a hose H which connects them. The receiver R for females, shown in FIG. 5, comprises a receiver frame 1' including a hollow element having an elliptical section, which is open at one end 1D' and has a hose coupling at the other end 1E'. It further includes a top grip or handle portion 1B' and a bottom stand 2', and an abutting member 6' which is mounted in the opening at said one end 1D' of the receiver frame and is pressed against the groin of the body. In the device for use by males, shown in FIG. 6, the receiver R is a hollow element having an elliptical section, which is open at one end 1D' and has a hose coupling at the other end 1E', with the provision of a top grip or handle portion 1B'. In use of the device for females, the user holds the top grip portion 1B' by one hand and applies the open end of the abutting portion 6' against the inguinal region about the urethral orifice. The receiver R is supported by the stand 2' on the bed. As to the device for males, the user holds the top grip portion 1B' by one hand and inserts the penis into the receiver R through the opening.

However, in the above known sanitary device for females, since the receiver R is abutted at its lower end against the body by a mere gripping hold on the top grip portion 1B, the point of action which is in line with the point of force must be displaced with a considerable force towards the body by generating a rotational moment at said point of force. Therefore, it is difficult to ensure close contact between the abutting portion 6' and the skin around the urethral orifice, and in particular the contact force (pressing force) at the lower part of the groin (near the hip) tends to become insufficient. The result is that the urine frequently leaks out at the lower part and soils the patient's clothes, the linen and the like.

In the case of the conventional device for males, the patient is required to hold the receiver by one hand in a fixed position with the hose coupling side lower than the other part, and the resulting exertion causes mental and physical fatigue.

Moreover, a nurse is required to wash the soiled abutting portion after each use and, also, to discard the urine when it accumulates to a certain level in the tank and wash the tank, the connecting hose, etc. Furthermore, the patient's clothes, linen, etc. which are soiled as described must be replaced with fresh ones and laundered.

These circumstances impose considerable mental and physical burdens on the patient at every urination.

It is a general object of the present invention to avoid the foregoing problems. More specifically, it is an object of the present invention to provide a sanitary device for a patient which can be easily used by the patient himself (or herself) with a minimum of exertion and without causing the urine to spill and soil the clothes, linen and so on, thus relieving the patient and the nurse of physical and mental burdens.

BRIEF SUMMARY OF THE INVENTION

A sanitary device according to the present invention comprises a urine receiver and a urine bag removably attached to the receiver. The urine receiver includes a receiver body forming an opening at least at both ends thereof, and adapted to accommodate the urine bag therein through the open ends. A receiver frame is adapted to rotatably support the receiver body by means of pivot pins and is equipped with grip means at a lower end thereof, adapted to press one side of the receiver body in abutment against the body of a user of the device. A grip handle portion is disposed at the upper end thereof. The urine bag is a hollow element having an opening at one end thereof and fitted with an elastic, hygroscopic abutting member configured to be complementary for the inguinal region of the body against which it is to be abutted, and it is adapted to be accommodated in the receiver body to thereby prevent leakage of urine during use of the device.

BRIEF DESCRIPTION OF THE DRAWINGS

The invention will be better understood from the following detailed description taken in conjunction with the accompanying figures of the drawings, wherein:

FIG. 1 is a perspective view showing a receiver of a sanitary device for use by females, according to an embodiment of the present invention;

FIG. 1A is an enlarged view showing a part of the structure of FIG. 1;

FIG. 2 is a perspective view showing a urine bag of the device;

FIG. 3 is a perspective view showing the receiver and the urine bag mounted thereon;

FIG. 4 is a plan view showing the construction of a fold-back portion of the urine bag; and FIG. 5 and FIG. 6 are perspective views showing prior art sanitary devices.

DETAILED DESCRIPTION OF THE DRAWINGS

Referring first to FIG. 1, a receiver R (which may be made, for example, of molded plastic) according to this invention generally consists of a receiver body 1 and a receiver frame 2 on which the receiver body 1 is pivotably supported. The receiver body 1 is a hollow element which is open at both ends and is formed in an approximately elliptical configuration. It includes a top rearward wall portion that is partially cut-away, and a hole 1a (shown in FIG. 1 behind hole 2a) for accepting a mounting pin 7 on each side of the cutaway. The front opening 1b of the receiver body 1 generally conforms geometrically to the shape of the female inguinal region.

The receiver frame 2 has the approximate shape in side elevation of the letter L. The lower part is bifurcated downwardly from an intermediate position of a grip handle 2B and forms two branches 2b which curve forwardly and then join again at the front bottom end 2h. The front bottom end 2h of the receiver frame is formed with a rounded forward edge as best shown in FIG. 1, and the edge is fitted with a slip-proof rubber cover 2c having an indented or toothed grip surface at its bottom. The rear bottom corners (corresponding to the corner of the letter L) of the branches 2b are formed with heels 2d. Consequently when a sanitary device according to this invention is set in position on a flat surface such as a bed, the floor or the like, the heels 2d cooperate with the forward end 2h to support the sanitary device in a freestanding vertical position.

The branches 2b of the lower part of the frame 2 may also include a height adjusting mechanism. Each branch is divided into upper and lower parts which are connected by a mortise-tenon joint 2e. The tenons may be vertically adjusted in the mortises and held in a selected position by a pin. Thus the mounting position (height) of the receiver body 1 may be adjusted as desired. Above the joints 2e there are provided mounting holes 2a in the branches for accepting the pins 7 used for pivotally attaching the receiver body 1 to the upper part of the branches.

The top (the grip handle 2B) of the receiver frame 2 is so shaped as to assist gripping it. Thus, the spatial relation of the grip portion 2B of receiver frame 2, the mounting holes 2a of receiver body 1 and the front bottom end 2h provided with the grip cover 2c, is such that, when viewed from the inguinal region, the mounting holes 2a are disposed rearwardly (toward the right in FIG. 1) of the grip means 2c, and the grip handle 2B is disposed above the mounting holes 2a.

The receiver frame 2 is further provided, on the grip handle 2B, with a hook 2f on which a cord 5 (FIG. 2) of a urine bag may be hung. Moreover, a torsion spring 8 is preferably wound around each mounting pivot pin 7, the pins 7, of course, acting as pivot points for rotation of the receiver body 1 with respect to the receiver frame 2. One end of each coil spring 8 is secured to the receiver body 1 and the other end is secured to the receiver frame 2, whereby the receiver body 1 thereby being constantly biased in a forwardly dropping direction (the direction indicated by the arrow X in FIG. 1) relative to the frame.

The receiver frame 2, to which the receiver body 1 is rotatably attached, is provided with a projecting stop 2g on each of the branches 2b near the mounting holes 2a. The stops 2g are formed by projections on the inner sides of the branches 2b, the projections being engageable with the rearward edges of the body 1, so that the receiver body 1 is urged into a position such that it is high at the front opening 1b (the side to be abutted against the body) and low at the rear end.

Referring to the urine bag P, which is illustrated in FIG. 2 and FIG. 3, a bag 3 with an opening at the forward end only is folded back over a distance of about 7 to 10 centimeters around the opening. The bag 3 is so formed that it is reduced in sectional area as indicated at 3c, adjacent a folded-back portion 3b, as best shown in FIG. 4, and an internally mounted hollow member 4 is affixed to this foldedback portion 3b of the bag. This affixing is effected by fusion, for example, as indicated at 3a, so that the urine bag may not be easily broken or be likely to be broken. The bag extends both forwardly and rearwardly from the internal hollow member 4. A cord 5 for opening and closing the bag is attached to the forward tip of the bag in a loop and is provided with a fastener T for closing the opening of the bag.

The geometry of the front opening of the hollow member 4 is generally complementary with the groin or inguinal region of the female body, just as is the front opening of the receiver body 1. In particular, the lower portion of the hollow member 4 is so formed that it projects at its lower bottom edge toward the body to establish a sealing engagement with the inguinal region. Further the front edge of the hollow member 4 is fitted with an abutting means 6 made of a flexible and hygroscopic material such as sponge, sanitary napkin material, or the like. The hollow member 4 is dimensioned so that when it is applied against the female groin when in use, the opening of hollow member 4 covers the entire region extending from above the urethral orifice to the region approaching the anus.

To put the sanitary device into use, the urine bag P is inserted through the opening 1A of the receiver body 1 and the folded back portion 3b of the bag P is folded back over and around the front edge of the receiver body 1 as shown in FIG. 3. Then, the end 5a of the loop of the cord for opening and closing the bag 3 is hooked on the hook 2f formed on the grip handle portion 2B of the receiver frame 2. By folding back the forward end of the bag, the forward edge of the hollow member 4 is exposed as shown in FIGS. 2 and 3 and the member 4 is held within the body 1.

The method of using the sanitary device of this invention is now described with reference to FIG. 3. First, the height of the receiver body 1 is adjusted; using the height-adjusting joint 2e (FIG. 1) to be commensurate with the physical build and other features of the use of the sanitary device. The user's legs are set a little apart and the sanitary device is positioned immediately in front of the inguinal region. Then the user holds the grip handle 2B of the receiver frame 2 with one hand and positions the bottom end (the heals 2d and the cover 2c) of the receiver frame 2 on the bed sheet so that the opening defined by an abutting rim portion 6 of the urine bag inserted into the receiver element 1 will cover the region extending from above the urethral orifice to the region adjoining the anus. Then, in this condition, the grip portion 2B is turned (swung) toward the user's stomach. As this is done, the receiver body 1 (abutted against the body) is not dislocated, for the receiver body 1 (holding the abutting portion 6) is tilted (swung on the pins 7) in the opposite direction in response to the rotation of the receiver frame 2. Further, the grip-proof cover 2c secures the lower end of the receiver frame firmly in position on the bed.

Moreover, since the front bottom end 2h of the receiver frame 2 is curved, the slip-proof cover 2c (which may be made of rubber) functions as a fulcrum as the receiver frame 2 is tilted toward the inguinal region. As a result, the lower part of the abutting portion of receiver frame 1 is displaced toward the body, thus adding to the abutting force (pressing force). As the grip portion 2B is further tilted toward the stomach, the receiver body 1 is pressed to the person's body by means of the abutting stops 2g adjacent the mounting pins 7. Therefore, when the grip handle portion 2B is turned counterclockwise (as seen in FIG. 1), a counterclockwise directed force is also generated at the front bottom end 2h of the receiver frame, with the result that a force with a rearward component and a downward component (towards the sheet or bed) acts on the front bottom end 2h. For this reason, the front bottom end 2h of receiver frame 2 is securely locked in position on the sheet. The front bottom end 2h, serving as fulcrum, and the abutting portion 2g, serving as points of action, are thus securely locked in position, and the abutting portion 6 is therefore secured intimately to the body. In this state, the front bottom end 2h of the receiver frame 2 functions as a fulcrum, the grip handle 2B as a point of force, and the abutting portion is a point of action; according to the principle of the lever, the pressing force at the grip handle 2B is amplified and acts upon the abutting portion 6 in proportion with the distance from the fulcrum to the point of force and the distance from the fulcrum to the point of action. Thus, this increased force coupled with the elasticity and groin-conforming shape of the abutting portion 6 establishes an intimate pressing contact between the person's body and the abutting portion 6, particularly at its lower edge. Since a large pressing force is thus obtained at the abutting portion 6 with a small force and the sanitary device is securely locked in position on the sheet as described hereinbefore, the front bottom portion 2h of the receiver frame can be forcefully pressed downward by pulling the grip handle 2B simply toward oneself without applying a downward force, with the result that even a patient who cannot make a great physical exertion can easily utilize the sanitary device without fatigue.

The bag with urine recovered therein can be simply dismounted from the receiver and discarded at a designated place for disposal. Thus, the patient can hygienically use the sanitary device repeatedly by attaching a new urine bag to the receiver after each urination and the nurse is also relieved of the labor required for cleaning the sanitary device after each use or changing the patient's clothes, linen, etc. and having them laundered.

Since the construction of the sanitary device according to the present invention is such that the abutting portion is swung about the lower end of the receiver frame and brought into contact with the body, even if the height of the urethral orifice varies according to the patient's physical build, it can readily be adapted to the variation over a fairly large range by changing the angle of rotation of the grip portion.

If urination is effected in such a manner, the urine will not leak out of the bag but will flow through the hollow member 4 into the bag 3 integrally formed with the member 4. Upon completion of urination, the urine collects in the bottom of the bag 3 which rests on the bed. Thereupon the patient releases her/his grip on the grip handle 2B, disengages the cord 5 from the hook 2f, pulls it up toward herself (himself), whereupon the receiver body 1 swings upward about the pivot pins 7 and, in the process, the folded part 3b of the bag 3 is automatically reversed or unfolded, thereby wrapping the abutting portion 6 up in the bag 3. Then, the top portion of the urine bag just behind the opening is closed with the cord and the fastener means T, whereby the bag is bent at the fastening position in the shape of the letter U and the opening is closed.

Then, the urine bag P is slipped out from the receiver R, removed from the bed, and, for example, hung on a hook (not shown) provided at the bed side. Thus, after urination, the abutting portion 6 is automatically wrapped into the sanitary bag without requiring the patient to touch it by hand and the bag is also tightly closed by the fastener cord. Therefore, there is no risk of the urine bag ever soiling the linen, etc. when it is carried away from the bed. Furthermore, since the top end of the urine bag can be closed liquid-tight with the fastener cord as mentioned above, the urine is not spilt on the bed, etc.

While the above description has been limited to use of the sanitary device by females, it will be obvious that the same sanitary device and bag can be used by males as well. When used by a male patient, it is not necessary to apply the abutting portion 6 of the device tightly against the inguinal region of the body, but it is sufficient to apply the lower edge of the abutting portion against the underside of the penis and to set the penis in position within the urine bag. As in the case of a female user, the height of the receiver body may be adjusted according to his physical build.

In the above embodiment of the invention, there may also be provided a cleaning liquid nozzle just above the receiver body and a switch on the grip handle of the receiver frame, so that the soiled body area around the urethral orifice can be washed clean. Moreover, if a transparent urine bag with volume graduations on it is used as the bag, the volume of urine from the patient can be measured at the same time.

Of course, the sanitary device according to the present invention can also be used in leisure activity situations such as when camping. In such applications, the use of an opaque urine bag is recommended.

As described above, with the sanitary device according to the present invention, the patient, if he (she) is able to move at least one of his (her) hands, can urinate by himself (herself) easily so that the dignity and privacy as a human being are not sacrificed. Moreover, this sanitary device can be used repeatedly without cleaning requiring only that the urine bag alone be replaced with a new one after each urination, and there is no risk of the patient's clothes, linen, etc. being soiled by spilt urine. As a result, the nurse is also relieved of the heavy labor for cleaning, laundering, etc. after each use of the device by the patient.

What is claimed is:

1. A sanitary device generally comprising a urine receiver and a urine bag means removably attached thereto, said urine receiver comprising a receiver body open at both ends thereof, said urine bag means being positioned in said receiver body and extending through said open ends, said receiver further comprising a receiver frame connected to rotatably support said receiver body by pivot pins, grip means at a lower end of said frame, and a grip handle portion disposed at the upper end thereof, said urine bag means comprising a hollow element open at one end thereof and fitted with an elastic, hygroscopic abutting member configured to be complementary for the inguinal region of the body against which it is to be abutted and adapted to be accommodated in said receiver body to thereby prevent leakage of urine during use of the device.

2. A sanitary device according to claim 1 wherein said receiver body is vertically adjustable in position with respect to said receiver frame.

3. A sanitary device according to claim 1 wherein said urine bag means is configured to be geometrically complementary for the shape of the inguinal region from just above the urethral orifice to a body region close to the anus.

4. A urine bag according to claim 1, and further including a cord extending around said bag adjacent said open end.

5. A urine bag for use with a receiver, comprising a hollow foldable bag having an opening at one open end thereof, a tubular member positioned within said bag adjacent but longitudinally spaced from said open end and generally coaxially with said open end, the outer periphery of said tubular member being sealingly connected to a portion of said bag which is spaced from said open end, and said tubular member having one end which is adjacent said open end of said bag and is generally complementary to the shape of the inguinal region of a person, said bag having one position where said bag extends beyond said one end of said tubular member and having a folded position where said open end is folded back and exposes said one end of said tubular member.

6. A frame for a urine collection bag, comprising a generally tubular body which is open at both ends thereof, said body having a top side, a bottom side opposite said top side and two laterally opposite sides, and said body being adapted to receive a bag, a frame including branches extending adjacent said laterally opposite sides of said body, heel pivot means connecting said laterally opposite sides of said body to said branches, a handle on said frame adjacent said top side and extending in one direction from said branches and away from said top side, and grip surface means on said frame and adjacent said bottom side and extending in the opposite direction from said branches.

7. A frame according to claim 6, wherein one end of said tubular body is shaped to engage a person, and said handle and said grip means are displaced from said pivot means in the direction of said are end.

8. A sanitary device generally comprising a urine receiver and a urine bag means removably attached thereto, said urine receiver comprising a receiver body open at both ends thereof, said urine bag means being positioned in said receiver body and extending through said open ends, said receiver further comprising a receiver frame connected to rotatably support said receiver body by pivot pins, grip surface means at a lower end of said frame, and a grip handle portion disposed at the upper end thereof, said urine bag means comprising a hollow element open at one end thereof, and fitted with a tubular member configured to be complementary for the inguinal region of the body against which it is to be abutted and adapted to be accommodated in said receiver body to thereby prevent leakage of urine during use of the device.

9. A sanitary device according to claim 8, wherein said receiver body is vertically adjustable in position with respect to said receiver frame.

10. A sanitary device according to claim 8, wherein said urine bag means is configured to be geometrically complementary for the shape of the inguinal region from just above the urethral orifice to a body region close to the anus.

11. A sanitary device according to claim 8, wherein said tubular member is an elastic hydroscopic member.

12. A urine bag according to claim 5, and further comprising a cord extending around said bag adjacent said open end.

* * * * *